United States Patent [19]
Nakamura et al.

[11] Patent Number: 5,393,627
[45] Date of Patent: Feb. 28, 1995

[54] PHOTOCONDUCTOR FOR ELECTROPHOTOGRAPHY

[75] Inventors: Yoichi Nakamura; Nobuyoshi Mori; Sumitaka Nogami, all of Kawasaki, Japan

[73] Assignee: Fuji Electric Co., Ltd., Kanagawa, Japan

[21] Appl. No.: 11,797

[22] Filed: Feb. 1, 1993

[30] Foreign Application Priority Data

Feb. 12, 1992 [JP] Japan ................. 4-024176

[51] Int. Cl.$^6$ ................. G03G 5/047; G03G 5/09
[52] U.S. Cl. ................. 430/59; 430/83
[58] Field of Search ................. 430/59, 83

[56] References Cited

U.S. PATENT DOCUMENTS

| | | |
|---|---|---|
| 3,189,447 | 6/1965 | Neugebauer et al. |
| 3,484,237 | 12/1969 | Shattuck et al. |
| 3,816,118 | 6/1974 | Byrne. |
| 4,150,987 | 4/1979 | Anderson et al. |
| 4,265,990 | 5/1981 | Stolka et al. ............ 430/59 |
| 4,278,747 | 7/1981 | Murayama et al. ....... 430/82 |
| 4,346,158 | 8/1982 | Pai et al. ................ 430/59 |
| 4,353,971 | 10/1982 | Chang et al. ............ 430/58 |
| 4,367,273 | 1/1983 | Murayama et al. ....... 430/56 |
| 4,385,106 | 5/1983 | Sakai ..................... 430/59 |
| 4,415,640 | 11/1983 | Goto et al. .............. 430/59 |
| 4,448,868 | 5/1984 | Suzuki et al. ............ 430/58 |
| 4,565,761 | 1/1986 | Katagiri et al. ........... 430/83 |
| 4,568,623 | 2/1986 | Makino et al. ........... 430/58 |
| 4,606,986 | 8/1986 | Yanus et al. ............. 430/59 |
| 4,624,904 | 11/1986 | Kazmaier et al. ........ 430/59 |
| 4,629,670 | 12/1986 | Katagiri et al. ........... 430/58 |
| 4,629,672 | 12/1986 | Makino et al. ........... 430/76 |
| 4,666,809 | 5/1987 | Matsumoto et al. ...... 430/76 |
| 4,673,630 | 6/1987 | Katagiri et al. ........... 430/72 |
| 4,677,045 | 6/1987 | Champ et al. ........... 430/76 |
| 4,702,983 | 10/1987 | Kazuhiro et al. ........ 430/75 |
| 4,731,315 | 3/1988 | Horie et al. ............. 430/77 |
| 4,783,387 | 11/1988 | Ueda ..................... 430/76 |

(List continued on next page.)

FOREIGN PATENT DOCUMENTS 0034942 9/1981 European Pat. Off. .

(List continued on next page.)

OTHER PUBLICATIONS

Johnson, R. N. et al., "Poly(aryl Ethers) by Nucleophilic Aromatic Substitution. I. Synthesis and Properties", *Journal of Polymer Science*, Part A-1, vol. 5, pp. 2375–2398 (1967).

(List continued on next page.)

*Primary Examiner*—Roland Martin
*Attorney, Agent, or Firm*—Spencer, Frank & Schneider

[57] ABSTRACT

The photoconductor for electrophotography comprises an electroconductive substrate and a photosensitive layer formed on the substrate. The photosensitive layer may be a monolayer or function-separated laminate type one which comprise a charge generating layer and a charge transporting layer laminated one on another. The charge transporting layer contains a specified diamine compound represented by general formula (I) below as the charge transporting substance.

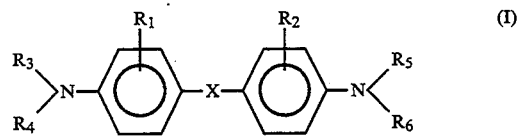

wherein $R_1$ and $R_2$, which are the same or different, each represent independently an alkyl group, an alkoxy group, or a halogen atom; $R_3$, $R_4$, $R_5$ and $R_6$, which are the same or different, each represent independently an aryl group or an alkyl group, or $R_3$ and $R_4$, or $R_5$ and $R_6$, combine and form a condensed aromatic ring; and X represents an oxygen atom, a sulfur atom, a carbonyl group, or a sulfonyl group.

8 Claims, 2 Drawing Sheets

U.S. PATENT DOCUMENTS

| | | | |
|---|---|---|---|
| 4,808,503 | 2/1989 | Yamada et al. | 430/75 |
| 4,839,252 | 6/1989 | Murata et al. | 430/59 |
| 4,861,691 | 8/1989 | Kuroda et al. | 430/59 |
| 4,861,692 | 8/1989 | Kuroda et al. | 430/59 |
| 4,865,934 | 9/1989 | Ueda et al. | 430/59 |
| 4,871,636 | 10/1989 | Hattori et al. | 430/77 |
| 4,877,703 | 10/1989 | Kuroda et al. | 430/76 |
| 4,882,255 | 11/1989 | Hattori et al. | 430/73 |
| 4,910,110 | 3/1990 | Kuroda et al. | 430/59 |
| 4,917,981 | 4/1990 | Nakamura et al. | 430/75 |
| 4,929,525 | 5/1990 | Kuroda et al. | 430/75 |
| 4,935,323 | 6/1990 | Hattori et al. | 430/58 |
| 4,945,021 | 7/1990 | Takata et al. | 430/76 |
| 4,948,689 | 8/1990 | Kuroda et al. | 430/59 |
| 4,950,572 | 8/1990 | Kuroda et al. | 430/59 |
| 4,954,405 | 9/1990 | Sugata et al. | 430/58 |
| 4,956,250 | 9/1990 | Kuroda et al. | 430/58 |
| 4,956,255 | 9/1990 | Ueda | 430/59 |
| 4,956,277 | 9/1990 | Kuroda et al. | 430/58 |
| 4,957,837 | 9/1990 | Kuroda et al. | 430/59 |
| 4,971,876 | 11/1990 | Kuroda | 430/75 |
| 4,985,325 | 1/1991 | Kuroda et al. | 430/59 |
| 4,988,594 | 1/1991 | Hattori et al. | 430/59 |
| 5,080,991 | 1/1992 | Ono et al. | 430/73 |
| 5,087,541 | 2/1992 | Kuroda et al. | 430/58 |
| 5,089,365 | 2/1992 | Kuroda et al. | 430/59 |
| 5,096,794 | 3/1992 | Kuroda et al. | 430/58 |
| 5,100,750 | 3/1992 | Kuroda et al. | 430/72 |
| 5,132,189 | 7/1992 | Kuroda et al. | 430/58 |
| 5,134,049 | 7/1992 | Kuroda et al. | 430/58 |
| 5,158,848 | 10/1992 | Kuroda et al. | 430/59 |
| 5,178,981 | 1/1993 | Hattori et al. | 430/58 |

FOREIGN PATENT DOCUMENTS

| | | |
|---|---|---|
| 0131140 | 1/1985 | European Pat. Off. . |
| 0270685 | 6/1988 | European Pat. Off. . |
| 1058836 | 6/1959 | Germany . |
| 1105714 | 4/1961 | Germany . |
| 1908343 | 8/1969 | Germany . |
| 1921273 | 11/1969 | Germany . |
| 2041490 | 3/1971 | Germany . |
| 2046914 | 8/1971 | Germany . |
| 2110971 | 12/1971 | Germany . |
| 2357851 | 6/1974 | Germany . |
| 2944949 | 6/1980 | Germany . |
| 3019909 | 11/1980 | Germany . |
| 3022545 | 1/1981 | Germany . |
| 3138292 | 5/1982 | Germany . |
| 3141306 | 6/1982 | Germany . |
| 3139524 | 8/1982 | Germany . |
| 3203621 | 9/1982 | Germany . |
| 3208337 | 9/1982 | Germany . |
| 3303830 | 8/1983 | Germany . |
| 3320674 | 12/1983 | Germany . |
| 3602987 | 10/1986 | Germany . |
| 3643341 | 6/1987 | Germany . |
| 3841207 | 6/1989 | Germany . |
| 3842253 | 6/1989 | Germany . |
| 10785 | 5/1972 | Japan . |
| 37543 | 12/1972 | Japan . |
| 25658 | 7/1973 | Japan . |
| 47344 | 7/1973 | Japan . |
| 66444 | 12/1973 | Japan . |
| 69332 | 7/1974 | Japan . |
| 10496 | 4/1975 | Japan . |
| 39952 | 4/1975 | Japan . |
| 10138 | 1/1977 | Japan . |
| 25638 | 2/1977 | Japan . |
| 27033 | 3/1978 | Japan . |
| 150128 | 11/1979 | Japan . |
| 138263 | 4/1980 | Japan . |
| 138264 | 4/1980 | Japan . |
| 138265 | 4/1980 | Japan . |
| 138266 | 4/1980 | Japan . |
| 153814 | 4/1980 | Japan . |
| 132965 | 9/1980 | Japan . |
| 42380 | 10/1980 | Japan . |
| 166557 | 11/1980 | Japan . |
| 12646 | 2/1981 | Japan . |
| 60443 | 5/1981 | Japan . |
| 104856 | 7/1981 | Japan . |
| 104857 | 7/1981 | Japan . |

PHOTOCONDUCTOR FOR ELECTROPHOTOGRAPHY

BACKGROUND OF THE INVENTION

1. FIELD OF THE INVENTION

The present invention relates to a photoconductor for electrophotography, and more particularly to a photoconductor for electrophotography which includes an electroconductive substrate having thereon a photosensitive layer containing a diamine compound.

2. DESCRIPTION OF THE PRIOR ART

Photosensitive materials conventionally used in photoconductors for electrophotography (hereafter, sometimes referred to simply as "photoconductors") include inorganic photoconductive substances such as selenium or selenium alloys, photoconductive materials containing inorganic photoconductive substances such as zinc oxide or cadmium sulfide dispersed in a binder resin, organic photoconductive substances such as poly-N-vinylcarbazole, or polyvinylanthracene, and organic photoconductive materials containing organic photoconductive substances such as phthalocyanin compounds or bisazo compounds dispersed in a binder resin or vacuum deposited on a suitable substrate. Photoconductors must have a function of maintaining surface charges in the dark, a function of generating charges upon receipt of light, and a function of transporting the generated charges upon receipt of light. There are two types of photoconductors, i.e., a monolayer type photoconductor which has all the above-mentioned functions in a single layer, and a laminated type one in which the above-mentioned functions are shared by a charge generating layer contributing mainly to generation of charges and a charge transporting layer contributing mainly to maintaining charges in the dark and transportation of charges upon receipt of light.

The electrophotographic image formation using these photoconductors is made, for example, according to the Carlson's method, in which a photoconductor is subjected in the dark to corona discharge to charge the photoconductor, the surface of the charged photoconductor is imagewise exposed to light using a manuscript or copy bearing, e.g., letters and/or pictures to form a latent electrostatic image, the thus formed latent electrostatic image is developed with a toner to form a visible image, the developed toner image is transferred to a support such as a paper sheet to fix the toner image on the support. After the toner image transfer, the photoconductor is subjected to the steps of removal of the electric charge and removal of the remaining toner (cleaning), and the like to be ready for reuse for a prolonged period of time.

Photoconductors for electrophotography utilizing organic materials have recently been studied and put into use because of their advantageous features such as flexibility, thermal stability, film-forming properties, and so on. Various charge transporting substances are known from, for example, U.S. Pat. No. 3,189,447 which discloses oxadiazole compounds, Japanese Patent Publication No. 2023/1984 pyrazoline compounds, Japanese Patent laying-open Nos. 42380/1980, 101844/1982, and 150128/1979 hydrazone compounds, respectively, as charge transporting substances.

Incidentally, many of the photoconductors currently put into practical use are of function-separated type and include a charge generating layer and a charge transporting layer. For example, Japanese Patent Publication No. 42380/1980 discloses a function-separated type photoconductor which uses chlorocyan blue as a charge generating substance and a hydrazone compound as a charge transporting substance. It is expected that this results in a photoconductor having a high sensitivity and a high durability. While organic materials have many advantages that inorganic materials do not have, there has been obtained no organic material that meets all the characteristics required for photoconductors for electrophotography. In particular, low durability is now at stake.

The decrease in durability is considered to be ascribable to decrease in sensitivity, increase in residual potential, decrease in chargeability, blurring of image, occurrence of white spots, or black spots, after prolonged use, as well as increase in residual potential, decrease in chargeability and mechanical wear of the surface of the photoconductor under the conditions of high temperature and high humidity, or low temperature and low humidity, and so on.

Deterioration of electric characteristics is considered to be ascribable to chemical deterioration of the charge transporting substance contained in the surface layer of the photoconductor, i.e., oxidation or photolysis with ozone, $NO_x$ or the like formed concomitantly with corona discharge. It is considered that physicochemical factors are also involved in the deterioration of electric characteristics. For example, crystallization and deposition of the charge transporting substance in the charge transporting layer, morphological change of the charge transporting substance between the interface of the charge generating, layer and the charge transporting layer.

Various trials have been made in order to increase the durability of photoconductors. For example, it has been proposed to add an ultraviolet absorbent or antioxidant in the photosensitive layer of the photoconductor, to develop binder resins having improved compatibilities with the charge transporting substance. However, further improvement is desired.

SUMMARY OF THE INVENTION

Under the circumstances, the present invention has been made, and it is an object of the present invention to provide a photoconductor which uses a novel charge transporting substance and has a high sensitivity that will not be deteriorated after repeated use for a long time.

As a result of extensive investigation, it has now been found that the above object can be achieved by the use of specified diamine compounds as a charge transporting substance. The present invention has been completed based on this discovery.

Therefore, according to the present invention, there is provided a photoconductor for electrophotography which comprises:

a substrate; and a photosensitive layer formed on the substrate, wherein the photosensitive layer contains a diamine compound represented by general formula (I):

wherein $R_1$ and $R_2$, which are the same or different, each represent independently an alkyl group, an alkoxy group, or a halogen atom; $R_3$, $R_4$, $R_5$ and $R_6$, which are the same or different, each represent independently an aryl group or an alkyl group, or $R_3$ and $R_4$, or $R_5$ and $R_6$, combine and form a condensed aromatic ring; and X represents an oxygen atom, a sulfur atom, a carbonyl group, or a sulfonyl group.

Here, the photosensitive layer may be of a laminate, function-separated photosensitive layer having a charge generating layer and a charge transporting layer. The photosensitive layer may also be of a monolayer.

The diamine compound represented by formula (I) may be one in which $R_1$ and $R_2$ are hydrogen atoms, respectively, and $R_3$, $R_4$, $R_5$ and $R_6$ are phenyl groups, respectively.

According to the present invention, the use of the diamine compound represented by general formula (I) as a charge transporting substance on an electroconductive substrate results in a photoconductor which has a high sensitivity and an excellent characteristics without suffering from increase in residual potential, decrease in charge potential, and deterioration of image.

The above and other objects, effects, features and advantages of the present invention will become more apparent from the following description of embodiments thereof taken in conjunction with the accompanying drawings.

DETAILED DESCRIPTION OF THE INVENTION

The photoconductor of the present invention, which contains the specified diamine compound as a charge transporting substance in the photosensitive layer thereof, may have any one of various known structures for photoconductors for electrophotography. The specified diamine compound will be explained in detail later on.

Usually, the photoconductor of the present invention may have any one of the structures shown in FIGS. 1 to 6.

FIGS. 1 to 6 are schematic cross sectional views showing photoconductors according to various embodiments of the present invention.

Figure 1:
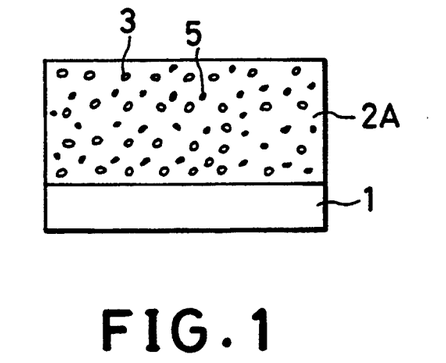
FIGS. 1 and 2 are schematic cross-sectional views showing monolayer photoconductors according to the present invention.

FIG. 1 is a cross sectional view showing a monolayer type photoconductor. A photosensitive layer 2A is provided on an electroconductive substrate 1. The photosensitive layer 2A comprises a charge generating substance 3, and the above-mentioned diamine compound as a charge transporting substance 5, both of which substances are dispersed in a resin binder matrix so that the photosensitive layer 2A functions as a photoconductor.

Figure 2:
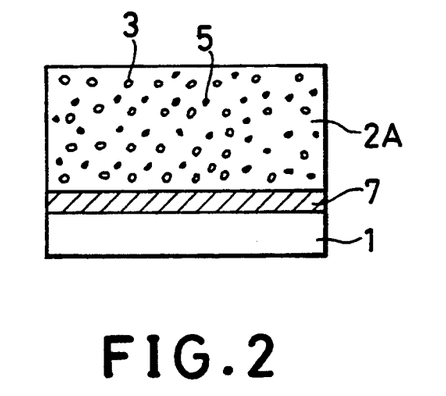

FIG. 2 is a cross sectional view showing another monolayer type photoconductor. The photoconductor shown in FIG. 2 differs from that shown in FIG. 1 in that the photosensitive layer 2A is provided on the substrate 1 via one or more intermediate layers 7 such as a subbing layer, a barrier layer, etc.

Figure 3:
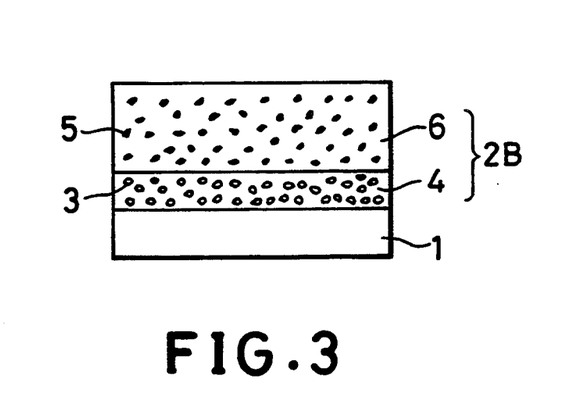
FIGS. 3 to 6 are schematic cross-sectional views showing function-separated laminate photoconductors according to the present invention.

FIG. 3 is a cross sectional view showing a laminate type photoconductor. A laminated photosensitive layer 2B is provided on an electroconductive substrate 1, in which a lower layer of the laminate is a charge generating layer 4 containing a charge generating substance 3, and an upper one is a charge transporting layer 6 containing the above-mentioned diamine compound as a charge transporting substance 5 as a main component, so that the photosensitive layer 2B functions as a photoconductor. This photoconductor is usually used according to the negative charge mode.

Figure 4:
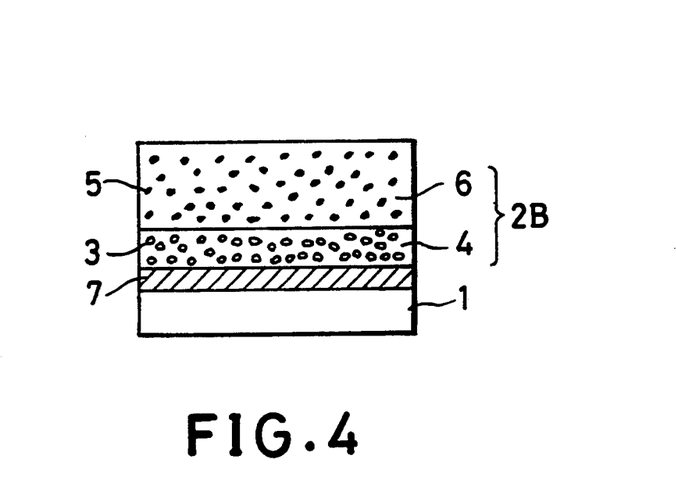

FIG. 4 is a cross sectional view showing another laminate type photoconductor shown in FIG. 3. The photoconductor shown in FIG. 4 differs from that shown in FIG. 3 in that the photosensitive layer 2B is provided on the substrate 1 via one or more intermediate layers 7 such as a subbing layer, a barrier layer, etc.

Figure 5:
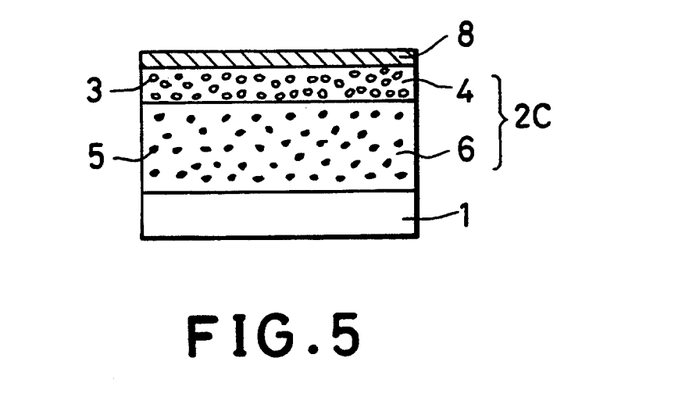

FIG. 5 is another laminate type photoconductor having a layer structure in reverse to that shown in FIG. 3. A laminated photosensitive layer 2C is provided on an electroconductive substrate 1, in which a lower layer of the laminate is a charge transporting layer 6 including the above-mentioned diamine compound as a charge transporting substance 5 as a main component, and an upper one is a charge generating layer 4 containing a charge generating substance 3, so that the photosensitive layer 2C functions as a photoconductor. This photoconductor is usually used according to the positive charge mode. In this case, a cover layer 8 may generally be further provided as shown in FIG. 5 to protect the charge generating layer 4.

Figure 6:
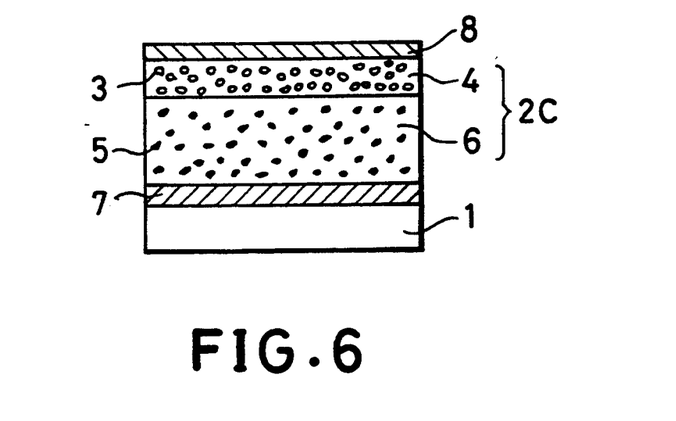

FIG. 6 is a cross sectional view showing another laminate type photoconductor shown in FIG. 5. The photoconductor shown in FIG. 6 differs from that shown in FIG. 5 in that the photosensitive layer 2C is provided on the substrate 1 via one or more intermediate layers 7 such as a subbing layer, a barrier layer, etc.

The photoconductors as shown in FIGS. 1 and 2, respectively, can be produced by dispersing a charge generating substance in a solution of a charge transporting substance and a resin binder and applying the resulting dispersion on an electroconductive substrate after optionally applying thereon one or more intermediate layers, and then drying the resulting coating film.

The photoconductors as shown in FIGS. 3 and 4 can be produced by applying on an electroconductive substrate a dispersion of a particulate charge generating substance in a solvent and/or a resin binder after optionally applying thereon one or more intermediate layers, applying the resulting dispersion on an electroconductive substrate, followed by applying a solution of a charge transporting substance and a binder resin, and then drying the resulting coating film.

The photoconductors as shown in FIGS. 5 and 6 can be produced by applying a solution of a charge transporting substance and a binder resin on an electroconductive substrate after optionally coating one or more intermediate layers, drying the resulting coating film, applying a dispersion of a particulate charge generating substance in a solvent and/or a resin binder, followed by drying the coating film.

The photosensitive layer in the photoconductor of the present invention contains a diamine compound represented by general formula (I):

(I)

wherein $R_1$ and $R_2$, which are the same or different, each represent independently an alkyl group, an alkoxy group, or a halogen atom; $R_3$, $R_4$, $R_5$ and $R_6$, which are the same or different, each represent independently an aryl group or an alkyl group, or $R_3$ and $R_4$, or $R_5$ and $R_6$, combine and form a condensed aromatic group; and X represents an oxygen atom, a sulfur atom, a carbonyl group, or a sulfonyl group.

In general formula (I), the alkyl group represented by $R_1$ and $R_2$ may have usually 1 to 8, preferably 1 to 4, carbon atoms, and include, for example, a methyl group, an ethyl group, a propyl group, a butyl group, a pentyl group, a hexyl group, a heptyl group, an octyl group. Preferred examples are an methyl group, an ethyl group, a propyl group, and a butyl group.

The alkoxy group represented by $R_1$ and $R_2$ may have usually 1 to 4, preferably 1 to 2 carbon atoms, and include, for example, a methoxy group, an ethoxy group, a propoxy group, and a butoxy group. Preferred examples include a methoxy group and an ethoxy group.

The halogen atom represented by $R_1$ and $R_2$ may include fluorine, chlorine, bromine, iodine, etc., with chlorine being preferred.

The aryl group represented by $R_3$, $R_4$, $R_5$ and $R_6$ may be a 5- or 6-membered ring having usually 3 to 14, preferably 3 to 10 carbon atoms, and include, for example, a phenyl group, a naphthyl group, a biphenyl group, etc. The aryl group may be substituted. The substituent may include, for example, a lower alkyl group having 1 to 8 carbon atoms, such as a methyl group, an ethyl group, a propyl group, a butyl group, etc., a lower alkoxy group having 1 to 4 carbon atoms, such as a methoxy group, an ethoxy group, etc.

The alkyl group represented by $R_3$, $R_4$, $R_5$ and $R_6$ may have usually 1 to 8, preferably 1 to 4, carbon atoms, and include, for example, a methyl group, an ethyl group, a propyl group, a butyl group, a pentyl group, a hexyl group, a heptyl group, and an octyl group. Preferred examples are a methyl group, an ethyl group, a propyl group, and a butyl group.

The condensed ring formed by $R_3$ and $R_4$, or $R_5$ and $R_6$, together with the nitrogen atom to which they are attached, may be a 5- to 14-membered heterocyclic ring, for example, indoline, 1,2,3,4-tetrahydroquinoline, carbazole, 9,10-dihydroacridine, etc.

Indoline:

1,2,3,4-Tetrahydroquinoline:

Carbazole:

9,10-Dihydroacridine:

These heterocyclic rings may be substituted with a lower alkyl group having 1 to 4 carbon atoms, such as a methyl group, an ethyl group, a propyl group, a butyl group, etc.

The diamine compound represented by general formula (I) include a bis(substituted-aminophenyl)ether type compound represented by general formula (IA):

(IA)

a bis(substituted-aminophenyl)thioether type compound represented by general formula (IB):

(IB)

a di(substituted-amino)benzophenone type compound represented by general formula (IC):

(IC)

a bis(substituted-aminophenyl)sulfone type compound represented by general formula (ID):

(ID)

Representative examples of the diamine compound represented by general formula (I) are listed as below.

TABLE 1

| COMPOUND | R₁ | R₂ | R₃ | R₄ | R₅ | R₆ |
|---|---|---|---|---|---|---|
| I$_A$-1 | —H | —H |  |  |  |  |
| I$_A$-2 | —H | —H |  |  |  |  |
| I$_A$-3 | —H | 2-OCH₃ |  |  |  |  |
| I$_A$-4 | —H | 2-OCH₃ |  |  |  |  |
| I$_A$-5 | —H | —H |  |  |  |  |
| I$_A$-6 | —H | —H |  | | |  |
| I$_A$-7 | —H | —H |  | | |  |
| I$_A$-8 | 3-CH₃ | 3-CH₃ |  |  |  |  |
| I$_A$-9 | 3-CH₃ | 3-CH₃ |  |  |  |  |
| I$_A$-10 | 3-CH₃ | 3-CH₃ |  | | |  |
| I$_A$-11 | 3-OCH₃ | 3-OCH₃ |  |  |  |  |
| I$_A$-12 | 3-OCH₃ | 3-OCH₃ |  |  |  |  |

TABLE 1-continued

| COMPOUND | R₁ | R₂ | R₃ | R₄ | R₅ | R₆ |
|---|---|---|---|---|---|---|
| I$_A$-13 | 3-OCH₃ | 3-OCH₃ |  | |  | |
| I$_A$-14 | —H | —H | —C₂H₅ | —C₂H₅ |  |  |
| I$_A$-15 | 3-Cl | 3-Cl |  |  |  |  |

TABLE 2

| COMPOUND | R₁ | R₂ | R₃ | R₄ | R₅ | R₆ |
|---|---|---|---|---|---|---|
| I$_B$-1 | —H | —H |  |  |  |  |
| I$_B$-2 | —H | —H |  |  |  |  |
| I$_B$-3 | —H | —H |  |  |  |  |
| I$_B$-4 | —H | —H |  |  |  |  |
| I$_B$-5 | —H | —H |  | |  | |
| I$_B$-6 | —H | —H |  | |  | |
| I$_B$-7 | —H | —H |  | |  | |
| I$_B$-8 | —H | —H |  |  |  |  |

TABLE 2-continued

| COMPOUND | R₁ | R₂ | R₃ | R₄ | R₅ | R₆ |
|---|---|---|---|---|---|---|
| I$_B$-9 | —H | —H | phenyl | naphthyl | phenyl | naphthyl |
| I$_B$-10 | —H | —H | carbazolyl | | carbazolyl | |
| I$_B$-11 | —H | —H | 1,2,3,4-tetrahydroquinolinyl | | 1,2,3,4-tetrahydroquinolinyl | |
| I$_B$-12 | —H | —H | —C$_2$H$_5$ | —C$_2$H$_5$ | phenyl | phenyl |
| I$_B$-13 | 3-Cl | 3-Cl | phenyl | phenyl | phenyl | phenyl |

TABLE 3

| COMPOUND | R₁ | R₂ | R₃ | R₄ | R₅ | R₆ |
|---|---|---|---|---|---|---|
| I$_C$-1 | —H | —H | phenyl | phenyl | phenyl | phenyl |
| I$_C$-2 | —H | —H | phenyl | 3-CH$_3$-phenyl | phenyl | 3-CH$_3$-phenyl |
| I$_C$-3 | —H | —H | 4-CH$_3$-phenyl | 4-CH$_3$-phenyl | 4-CH$_3$-phenyl | 4-CH$_3$-phenyl |
| I$_C$-4 | —H | —H | phenyl | 3-OCH$_3$-phenyl | 3-OCH$_3$-phenyl | phenyl |
| I$_C$-5 | —H | —H | 4-CH$_3$-phenyl | 3-C$_4$H$_9$-phenyl | 4-CH$_3$-phenyl | 3-C$_4$H$_9$-phenyl |
| I$_C$-6 | —H | —H | carbazolyl | | carbazolyl | |
| I$_C$-7 | —H | —H | indolinyl | | indolinyl | |

TABLE 3-continued

| COMPOUND | R₁ | R₂ | R₃ | R₄ | R₅ | R₆ |
|---|---|---|---|---|---|---|
| I_C-8 | —H | —H | 3-methylindoline | | | indoline |
| I_C-9 | —H | —H | phenyl | biphenyl | phenyl | biphenyl |
| I_C-10 | —H | —H | phenyl | naphthyl | phenyl | naphthyl |
| I_C-11 | —H | —H | —C₂H₅ | —C₂H₅ | phenyl | phenyl |
| I_C-12 | 3-Cl | 3-Cl | phenyl | phenyl | phenyl | phenyl |

TABLE 4

| COMPOUND | R₁ | R₂ | R₃ | R₄ | R₅ | R₆ |
|---|---|---|---|---|---|---|
| I_D-1 | —H | —H | phenyl | phenyl | phenyl | phenyl |
| I_D-2 | —H | —H | phenyl | 3-methylphenyl | phenyl | 3-methylphenyl |
| I_D-3 | —H | —H | phenyl | 3-methoxyphenyl | 3-methoxyphenyl | phenyl |
| I_D-4 | —H | —H | 3-methylphenyl | 4-methylphenyl | 4-methylphenyl | 3-methylphenyl |
| I_D-5 | —H | —H | indoline | | | indoline |
| I_D-6 | —H | —H | phenyl | biphenyl | phenyl | biphenyl |

TABLE 4-continued

| COMPOUND | R₁ | R₂ | R₃ | R₄ | R₅ | R₆ |
|---|---|---|---|---|---|---|
| I_D-7 | —H | —H |  |  |  |  |
| I_D-8 | —H | —H | —C₂H₅ | —C₂H₅ |  |  |
| I_D-9 | 3-Cl | 3-Cl |  |  |  |  |

As described above, the photoconductor for electrophotography according to the present invention has a photosensitive layer on an electroconductive substrate.

Various materials can be used as the electroconductive substrate. For example, there can be used metals such as iron, nickel, copper and aluminum, metal-deposited plastic films, electroconductive plastics, and the like. These can be in any form including sheet, belt, cylinder, etc. As necessary, one or more intermediate layers such as an electroconductive subbing layer, a barrier layer or the like may be provided on the electroconductive substrate.

The photosensitive layer, which is provided on the electroconductive substrate directly or via one or more intermediate layers, may be a monolayer photosensitive layer which is provided by dispersing and dissolving a charge generating substance and a charge transporting substance in a binder and applying the resulting dispersion on the substrate. Alternatively, the photosensitive layer may be a function-separated laminate photosensitive layer which is provided by applying a charge generating layer containing a charge generating substance and a charge transporting layer containing a charge transporting substance separately adjacent to each other.

The diamine compound used as a charge transporting substance in the present invention can be applied in the both types of the photoconductors. It is preferred to use the diamine compound as a charge transporting substance in function-separated type photoconductors When it is used in a monolayer photosensitive layer, the charge generating substance which can be used include selenium, selenium-tellurium, amorphous silicon, polycrystalline silicon, pyrylium salts, squarylium salts, pyrrolopyrrole compounds, anthanthrone compounds, perylene compounds, disazo compounds, phthalocyanine compounds, etc. These can be used singly or two or more of them can be used in combination. The charge generating substance and the charge transporting substance represented by general formula (I) above are dispersed and dissolved in a suitable binder. The charge transporting substance need not be limited to the diamine compounds but those charge transporting substances other than the above-mentioned diamine compounds, such as hydrazone compounds and fluorenone compounds as disclosed in Japanese Patent Application Laid-Open No. 1151/1991, can be added in addition. The amount of the charge transporting substances other than the diamine compounds may be added up to 90% by weight based on the total weight of the charge transporting substances. The diamine compounds represented by general formula (I) above may be used singly or in combination of two or more of them.

The charge generating substance and charge transporting substance can be used together with various binder resins, for example, polystyrenes, acrylic resins, ethylene copolymers, polyvinyl chlorides, polyesters, polyamides, polyurethanes, epoxy resins, polyarylates, polycarbonates, polyethers, silicone resins, etc. Polystyrenes, poly(meth)acrylates, polyesters, and polycarbonates are used practically in most cases.

When the photoconductor is formed as a monolayer photoconductor, there can be used 2 to 20 parts by weight, preferably 3 to 15 parts by weight, of the charge generating substance, and 40 to 200 parts by weight, preferably 50 to 100 parts by weight, of the charge transporting substance, per 100 parts by weight of the binder resin. The binder, charge generating substance, charge transporting substance, and optionally an antioxidant, an ultraviolet absorbent, and a leveling agent are dispersed in a solvent such as tetrahydrofuran, methyl ethyl ketone, dioxane, acetone, dichloromethane, or dichloroethane using a conventional disperser such as a ball mill, a paint shaker, a sand mill, or an attritor. The resulting dispersion can be coated to a thickness of 10 to 50 μm (dry basis) by a conventional coating method such as spraying, dipping, curtain flow coating, or screen coating.

In the case of a function-separated photoconductor having a charge generating layer and a charge transporting layer separately, the photosensitive layer is composed of a charge generating layer and a charge transporting layer.

The charge transporting layer, which is provided adjacent to the charge generating layer, is formed by dissolving the diamine compound represented by general formula (I) together with a suitable binder resin, such as polyester, polycarbonate, polyurethane, acrylic resin, polystyrene or the like, in a suitable solvent, and coating and drying the resulting solution. Specific examples of the suitable solvent which can be used include alcohols such as methanol, ethanol, and butanol; ketones such as acetone, methyl ethyl ketone, methyl isobutyl ketone, and cyclohexanone; ethers such as tetrahydrofuran, dioxane, and ethylene glycol monomethyl ether; esters such as methyl acetate, ethyl acetate; halogenated hydrocarbons such as chloroform, dichloromethane, dichloroethane, dichloroethylene, and trichloroethane; and aromatic hydrocarbons such as toluene, xylene, and dichlorobenzene. The proportion of the diamine compound represented by general formula (I) is 10 to 500 parts by weight, preferably 50 to 200 parts by weight, per 100 parts by weight of the binder resin. It is suitable that the charge transporting layer has a thickness of 10 to 100 μm, preferably 20 to 50 μm. The coating can be performed by spraying, dipping, roll coating, or the like. The charge transporting layer may contain various additives such as an ultraviolet absorbent, an antioxidant, etc.

For the charge generating layer, the charge generating substances which can be used include inorganic substances such as selenium, selenium-tellurium, and selenium arsenide, and organic pigments such as azo pigments, anthanthrone pigments, and phthalocyanine pigments. The charge generating layer can be formed by vapor deposition or coating. The coating can be performed by dispersing the above-mentioned charge generating substance in a binder and applying the resulting dispersion on an electroconductive substance. Examples of the resin which can be used advantageously as a binder include polyvinylformals, polyvinylacetals, polyvinylbutyrals, phenoxy resins, polyesters, polycarbonates, epoxy resins, vinyl chloride copolymers, etc. The content of the binder in the charge generating layer is suitably 60% by weight or less, preferably 50% by weight or less, and 10% by weight or more, preferably 30% by weight or more. The charge generating substance and the binder resin are dispersed together with a solvent for the binder resin using a conventional disperser such as a sand mill, a paint shaker or an attritor, and the resulting dispersion is coated to a thickness of, for example, 3 μm or less, preferably 0.01 to 2 μm. The electroconductive substrate on which the photosensitive layer is provided may be in the form of a sheet or drum, for example. It may be made of various materials such as metal-deposited or plated plastic films, metals such as aluminum, nickel, copper, and iron, and the like. As necessary, one or more intermediate layers such as an electroconductive subbing layer, a barrier layer or the like may be provided on the electroconductive substrate.

The resin which can be used for forming a subbing layer includes thermoplastic resins such as polyamides, polyesters, and vinyl chloride/vinyl acetate copolymers, or thermosetting resin, for example, a thermosetting resin obtained by thermal polymerization of a compound having a plurality of active hydrogen atoms (i.e., hydrogen in —OH group, —NH$_2$ group, —NH group, etc.) together with a compound having a plurality of isocyanate groups and/or a compound having a plurality of epoxy groups, and polyvinyl alcohol. The thickness of the subbing layer may be 0.05 to 10 μm, preferably 0.05 to 5 μm.

The barrier layer 7 may be composed of casein, polyvinyl alcohol, nitrocellulose, ethylene/acrylic acid copolymer, polyamides (nylon-6, nylon-66, nylon-610, copolymer nylons, alkoxymethylated nylons, etc.), polyurethanes, gelatin, or the like.

The thickness of the barrier may be 0.1 to 5 μm, preferably 0.5 to 3 μm.

The cover layer 8 is made of an organic insulating film forming material such as polyester, polyamide or the like which may contain an inorganic material such as SiO$_2$, an electric resistance-lowering material such as a metal or a metal oxide, or the like. The thickness of the cover layer may be 0.05 to 10 μm, preferably 0.05 to 5 μm.

The charge transporting substance used in the present invention has an excellent compatibility with various binder resins.

The diamine compound represented by general formula (I) can be prepared by reacting a compound represented by general formula (II) below:

wherein $R_1$, $R_2$ and X have the same meanings as defined above; and Y represents a halogen atom, with a secondary diamine compound represented by general formula (III)

wherein $R_7$ and $R_8$ each represent an aryl group or an alkyl group, or $R_7$ and $R_8$ combine and form a condensed aromatic ring; and X represents an oxygen atom, a sulfur atom, a carbonyl group, or a sulfonyl group.

The secondary diamine compound represented by general formula (III) typically includes, for example, dialkyl secondary amines, aromatic secondary amines and condensed aromatic secondary amines.

The alkyl group represented by $R_7$ and $R_8$ may have usually 1 to 8, preferably 1 to 4, carbon atoms, and include, for example, a methyl group, an ethyl group, a propyl group, a butyl group, a pentyl group, a hexyl group, a heptyl group, and an octyl group. Preferred examples are a methyl group, an ethyl group, a propyl group, and a butyl group.

The aryl group represented by $R_7$ and $R_8$ may be a 5- to 14-membered ring having usually 3 to 14, preferably 3 to 10 carbon atoms, and include, for example, a phenyl group, a naphthyl group, a biphenyl group, etc., with a phenyl group being preferred. The aryl group may be substituted. The substituent may include, for example, a lower alkyl group having 1 to 8 carbon atoms, such as a methyl group, an ethyl group, a propyl group, a butyl group, etc., a lower alkoxy group having 1 to 4 carbon atoms, such as a methoxy group, an ethoxy group, etc.

The condensed aromatic secondary amines represented by $R_7$ and $R_8$ when taken together with the nitrogen atom to which they are attached include carbazole, 9,10-dihydroacridine, indoline, 1,2,3,4-tetrahydroquinoline, etc.

The reaction of the compound represented by general formula (II) with the secondary diamine compound represented by general formula (III) can proceed in a solvent such as sulfolane at a temperature of between 50° C. and 300° C. for 1 to 12 hours. In the reaction, copper chloride and copper oxide may be used as a catalyst.

EXAMPLES

Hereafter, the present invention will be described in more detail by examples. However, the invention should not be construed as being limited thereto.

Preparation Example

Preparation of Compound $I_B$-1

In a 1,000 ml three-necked flask were charged 22.2 g of 4,4'-difluorophenyl sulfide, 33.8 g of diphenylamine, 45 g of anhydrous potassium carbonate, 6 g of copper powder and 300 ml of sulfolane, and the mixture was heated at 240° C. for 24 hours with stirring under nitrogen atmosphere. After completion of the reaction, the reaction mixture was cooled, and water was added thereto, followed by stirring under reflux. Water was removed by decantation. Then, methanol was added to the residue and solids were washed by heating under reflux. In order to accelerate the reaction, copper chloride or copper oxide may be used as a catalyst in addition to the copper powder. After filtration, the residue was extracted with a mixed solvent of toluene/n-hexane, and the extract was purified by column chromatography.

The molecular weight of the objective compound was measured using a mass spectrometer FDMS (JMS-AX500) produced by Nippon Denshi Co., Ltd. The molecular weight determined was 316.

Elemental analysis was also conducted. Results are shown in Table 5 below.

TABLE 5

|  | Elemental Analysis | | | |
| --- | --- | --- | --- | --- |
|  | C % | H % | N % | S % |
| Found | 83.3 | 5.1 | 4.9 | 6.7 |
| Calculated | 83.8 | 5.4 | 4.6 | 6.2 |

Other compounds included by the diamine compound represented by general formula (I) can be prepared similarly.

Example 1

A mirror ground aluminum cylinder of a size of 60 mm in outer diameter, 348 mm in length and 1 mm in thickness was dip-coated with a 3% methanol solution of a polyamide (AMILAN CM-8000, produced by Toray Corporation) to form a subbing layer of 0.2 μm in thickness.

Then 21 parts by weight of a bisazo pigment represented by formula (IV) below:

(IV)

and 0.6 part by weight of a polyvinyl acetal (ESLEX KS-1, produced by Sekisui Chemical Industry Co., Ltd.) together with 9 parts by weight of cyclohexanone were dispersed using a paint shaker, and let down with a coating liquid consisting of 0.3 parts by weight of KS-1 and 75 parts by weight of methyl ethyl ketone to obtain a coating composition.

This coating composition was dip-coated on the aluminum cylinder provided with the subbing layer described above to form a charge generating layer of a dry thickness of 0.4 μm.

Next, a solution of 10 parts by weight of aliamine compound IB-1 above as a charge transporting substance, 10 parts by weight of a polycarbonate (UPIRON PCZ-300, produced by Mitsubishi Gas Chemical Co., Ltd.) in 80 parts by weight of dichloromethane was coated on the charge generating layer to form a charge transporting layer of a dry thickness of 25 μm, thus fabricating a photoconductor.

The photoconductor was attached to a commercially available copier (FP-3270, produced by Matsushita Electric Co., Ltd.) and the electrophotographic characteristics thereof were evaluated.

The initial potentials in the dark and in the light of the photoconductor were set to −800 V and −100 V, respectively, and sensitivity was defined by light volume (lx.s) from the potential in the dark to the potential in the light. The potential after exposure to light and after irradiating light in a light volume of 10 (lx.s) was defined as residual potential $V_r$. This procedure was followed for 10 hours continuously, and the characteristics were measured and changes in the image quality were observed.

As a result, the initial sensitivity was 1.0 lx.s, sensitivity after 10 hours 1.1 lx.s, initial Vr 12 V, and Vr after 10 hours 15 V. Thus, it was confirmed that both initial image quality and image quality after 10 hours were good.

Examples 2-6

Photoconductors were each fabricated and evaluated in the same manner as in Example 1 except that the charge transporting substance in Example 1 was replaced by one of compounds $I_A$-2, $I_C$-1, $I_C$-7, $I_D$-1, and $I_D$-3.

Results obtained are shown in Table 6 below.

TABLE 6

| | Initial | | | After 10 Hours | | |
| --- | --- | --- | --- | --- | --- | --- |
| Example | Sensitivity (lx · s) | Vr (V) | Image Quality | Sensitivity (lx · s) | Vr (V) | Image Quality |
| 2 | 1.2 | −10 | Good | 1.1 | −14 | Good |
| 3 | 1.1 | −13 | Good | 1.0 | −16 | Good |
| 4 | 1.4 | −18 | Good | 1.2 | −25 | Good |
| 5 | 1.7 | −20 | Good | 1.5 | −29 | Good |
| 6 | 1.3 | −14 | Good | 1.1 | −15 | Good |

From the results shown in Table 6 above, it was confirmed that both initial image quality and image quality after 10 hours were good.

Comparative Examples 1-3

Photoconductors were each fabricated and evaluated in the same manner as in Example 1 except that the charge transporting substance was replaced by one of compounds represented by formula (V), (VI) and (VII).

Results obtained are shown in Table 7 below.

TABLE 7

| Comparative Example | Initial | | | After 10 Hours | | |
|---|---|---|---|---|---|---|
| | Sensitivity (lx · s) | Vr (V) | Image Quality | Sensitivity (lx · s) | Vr (V) | Image Quality |
| 1 | 3.5 | −40 | Good | 5.5 | −120 | Fog |
| 2 | 2.8 | −30 | Good | 7.0 | −190 | Severe fog |
| 3 | 1.9 | −25 | Good | 2.6 | −70 | Fog |

From the results shown in Table 7 above, it can be seen that although initial image quality was good, sensitivity decreased, residual potential increased and image quality after 10 hours was poor since fog occurred.

Examples 7 and 8

A 3% methanol solution of a copolyamide (AMILAN CM/8000, produced by Toray Corporation) was dip-coated on an aluminum cylinder of a size of 60 mm in outer diameter, 1 mm in thickness, and 247 mm in length, having a mean surface roughness Rz=1.2 μm to provide a subbing layer of a dry thickness of 0.3 μm. Then, 1 part by weight of X type metal-free phthalocyanine (Fastogen Blue-8120B, produced by Dainippon Ink and Chemicals Inc.) and 1 part by weight of vinyl chloride copolymer (MR-110, produced by Nippon Zeon Co., Ltd.) were dispersed in 100 parts by weight of methylene chloride using a paint shaker to form a coating liquid. The coating liquid was dip-coated on the subbing layer provided on the aluminium cylinder described above to a dry thickness of 0.5 μm to form a charge generating layer. Next, a coating composition was prepared by dissolving 10 parts by weight of compound $I_A$-5 (Example 7) or $I_C$-2 (Example 8) as a charge generating transporting substance and 10 parts by weight of a polycarbonate (UPIRON PCZ-300, produced by Mitsubishi Gas Chemical Co., Ltd.) in 80 parts by weight of methylene chloride. The coating composition obtained was dip-coated on the charge generating layer to form a charge transporting layer of a dry thickness of 25 μm, thus producing a photoconductor.

Comparative Examples 4 to 6

Photoconductors were each fabricated in the same manner as in Example 7 except that the charge transporting substance in Example 7 was replaced by the charge transporting substance used in Comparative Example 1, 2 or 3.

Evaluation of Photoconductors

The photoconductors according to Examples 7 and 8 and Comparative Examples 4 to 7 were evaluated as follows. That is, the photoconductor was attached to a photoconductor process tester, electrified to −60 V using a corotton, rotated at a peripheral speed of 78.5 mm/sec, irradiated with a light at an exposure wavelength of 780 nm at an intensity of 2 μ/cm², and measured for an illuminated potential (Vi) after 0.2 second from the irradiation and a residual potential (Vr) after 1.5 second from the irradiation. Also, the potential in the dark (V₀) was measured Further, this procedure was repeated 5,000 times and changes in the characteristics were measured. Results obtained are shown in Tables 8 and 9 below.

TABLE 8

| Example | Initial | | | After 5000 Times | | |
|---|---|---|---|---|---|---|
| | $V_0$ (V) | $V_i$ (V) | $V_r$ (V) | $V_0$ (V) | $V_i$ (V) | $V_r$ (V) |
| 7 | −580 | −30 | −2 | −570 | −40 | −4 |
| 8 | −570 | −20 | −1 | −570 | −30 | −3 |

TABLE 9

| Comparative Example | Initial | | | After 5000 Times | | |
|---|---|---|---|---|---|---|
| | $V_0$ (V) | $V_i$ (V) | $V_r$ (V) | $V_0$ (V) | $V_i$ (V) | $V_r$ (V) |
| 4 | −600 | −100 | −50 | −550 | −150 | −70 |
| 5 | −610 | −110 | −60 | −530 | −180 | −80 |
| 6 | −600 | −80 | −20 | −560 | −120 | −50 |

As will be apparent from the results shown in Tables 8 and 9 above, the photoconductors containing the diamine compounds represented by general formula (I) above as a charge transporting substance had stable characteristics even after 5,000 times repeated operation.

The present invention has been described in detail with respect to preferred embodiments, and it will now be apparent from the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. A photoconductor for electrophotography, comprising:
   an electroconductive substrate; and
   a photosensitive layer which is a monolayer formed on the electroconductive substrate and which contains a charge generating substance, a charge transporting substance, and a binder resin, the charge generating substance and the charge transporting substance being dispersed in the binder resin;

wherein the charge transporting substance consists of a diamine compound represented by a general formula (I)

where $R_1$ and $R_2$, which are the same or different, each represent independently an alkyl group, an alkoxy group, or a halogen atom; where $R_3$ and $R_4$, or $R_5$ and $R_6$, combine together with a nitrogen atom to which they are bonded and form a 5- to 14-membered monocyclic heterocyclic ring having a nitrogen atom as a hetero atom and being condensed with one or two benzene rings; where X is an oxygen atom, a sulfur atom, a carbonyl group, or a sulfonyl group; and wherein the charge generating substance is a bisazo pigment represented by a formula (IV) below 2. The photoconductor for electrophotography as claimed in claim 1, wherein the diamine compound is a compound represented by the general formula (I) in which $R_3$ and $R_4$, or $R_5$ and $R_6$, combine together with a nitrogen atom to which they are bonded and form a heterocyclic ring selected from the group consisting of an indoline ring, a 1,2,3,4-tetrahydroquinoline ring, and a 9, 10-dihydroacridine ring.

3. A photoconductor for electrophotography, comprising:
an electroconductive substrate; and
a photosensitive layer which is a monolayer formed on the electroconductive substrate and which contains a charge generating substance, a charge transporting substance, and a binder resin, the charge generating substance and the charge transporting substance being dispersed in the binder resin;
wherein the charge transporting substance consists of a diamine compound represented by general a general formula (I)

where $R_1$ and $R_2$, which are the same or different, each represent independently an alkyl group, an alkoxy group, or a halogen atom; where $R_3$ and $R_4$, or $R_5$ and $R_6$, combine together with a nitrogen atom to which they are bonded and form a 5- to 14-membered monocyclic heterocyclic ring having a nitrogen atom as a hetero atom and being condensed with one or two benzene rings; where X is an oxygen atom, a sulfur atom, a carbonyl group, or a sulfonyl group; and wherein the charge generating substance is an X-type metal free phthalocyanine.

4. The photoconductor for electrophotography as claimed in claim 3, wherein the diamine compound is a compound represented by the general formula (I) in which $R_3$ and $R_4$, or $R_5$ and $R_6$, combine together with a nitrogen atom to which they are bonded and form a heterocyclic ring selected from the group consisting of an indoline ring, a 1,2,3,4,-tetrahydroquinoline ring, a carbazole ring, and a 9,10-dihydroacridine ring.

5. A photoconductor for electrophotography, comprising:
an electroconductive substrate; and
a photosensitive layer which is a laminate formed on the electroconductive substrate and which includes a charge generating layer containing a charge generating substance, and a charge transporting layer containing a charge transporting substance;
wherein the charge transporting substance consists of a diamine compound represented by a general formula (I)

where $R_1$ and $R_2$, which are the same of different, each represent independently an alkyl group, an alkoxy group, or a halogen atom; where $R_3$ and $R_4$, or $R_5$ and $R_6$, combine together with a nitrogen atom to which they are bonded and form a monocyclic aromatic ring having a nitrogen atom as a hetertto atom and being condensed with one or two benzene rings; where X is an oxygen atom, a sulfur atom, a carbonyl group, or a sulfonyl group; and wherein the charge generating substance is a bisazo pigment represented by a formula (IV) below (IV)

6. The photoconductor for electrophotography as claimed in claim 5, wherein the diamine compound is a compound represented by the general formula (I) in which $R_3$ and $R_4$, or $R_5$ and $R_6$, combine together with a nitrogen atom to which they are bonded and form a heterocyclic ring selected from the group consisting of an indoline ring, a 1,2,3,4-tetrahydroquinoline ring, a carbazole ring, and a 9,10-dihydroacridine ring.

7. A photoconductor for electrophotography, comprising:
an electroconductive substrate; and
a photosensitive layer which is a laminate formed on the electroconductive substrate and which includes a charge generating layer containing a charge generating substance, and a charge transporting layer containing a charge transporting substance;
wherein the charge transporting substance consists of a diamine compound represented by a general formula (I)

where $R_1$ and $R_2$ which are the same or different, each represent independently an alkyl group, an alkoxy group, or a halogen atom; where $R_3$ and $R_4$, or $R_5$ and $R_6$, combine together with a nitrogen atom to which they are bonded and form a monocyclic aromatic ring having a nitrogen atom as a hetero atom and being condensed with one or two benzene rings; and where X is an oxygen atom, a sulfur atom, a carbonyl group, or a sulfonyl group; and
wherein the charge generating substance is an X-type metal free phthalocyanine 8. The photoconductor for electrophotography as claimed in claim 7, wherein the diamine compound is a compound represented by the general formula (I) in which $R_3$ and $R_4$, or $R_5$ and $R_6$, combine together with a nitrogen atom to which they are bonded and form a heterocyclic ring selected from the group consisting of an indoline ring, a 1,2,3,4-tetrahydroquinoline ring, a carbazole ring, and a 9,10-dihydroacridine ring.

* * * * *